US007427391B2

(12) United States Patent
Lauenstein et al.

(10) Patent No.: US 7,427,391 B2
(45) Date of Patent: Sep. 23, 2008

(54) FORMULATIONS FOR USE IN MEDICAL AND DIAGNOSTIC PROCEDURES

(75) Inventors: Thomas C. Lauenstein, Essen (DE); Jorg F. Debatin, Essen (DE); Hubert Schneeman, Schermbeck (DE)

(73) Assignee: E-Z-Em, Inc., Lake Success, NY (US)

( * ) Notice: Subject to any disclaimer, the term of this patent is extended or adjusted under 35 U.S.C. 154(b) by 431 days.

(21) Appl. No.: 10/476,314

(22) PCT Filed: Nov. 21, 2002

(86) PCT No.: PCT/US02/37385

§ 371 (c)(1),
(2), (4) Date: Oct. 24, 2003

(87) PCT Pub. No.: WO03/045308

PCT Pub. Date: Jun. 5, 2003

(65) Prior Publication Data
US 2004/0241093 A1 Dec. 2, 2004

Related U.S. Application Data

(60) Provisional application No. 60/332,074, filed on Nov. 21, 2001.

(51) Int. Cl.
*A61K 49/00* (2006.01)
(52) U.S. Cl. .................. 424/9.1; 424/1.11; 424/1.73; 424/1.65; 424/9.3; 424/9.4
(58) Field of Classification Search ............ 424/1.11, 424/1.13, 1.21, 1.29, 1.65, 1.73, 9.1, 400, 424/450, 484, 485, 496; 514/937
See application file for complete search history.

(56) References Cited

U.S. PATENT DOCUMENTS

| | | |
|---|---|---|
| 3,975,512 A | 8/1976 | Long |
| 4,074,709 A | 2/1978 | Kaplan |
| 4,215,103 A | 7/1980 | Millington |
| 4,448,207 A | 5/1984 | Parrish |
| 4,930,997 A | 6/1990 | Bennett |
| 4,957,486 A | 9/1990 | Davis |
| 5,019,059 A | 5/1991 | Goldberg et al. |
| 5,107,842 A * | 4/1992 | Levene et al. ............... 424/9.5 |
| 5,131,906 A | 7/1992 | Chen |
| 5,645,816 A * | 7/1997 | Unger .................. 424/9.34 |
| 5,779,662 A | 7/1998 | Berman |
| 5,783,171 A * | 7/1998 | Gustavson et al. .......... 424/1.73 |
| 6,066,139 A | 5/2000 | Ryan et al. |
| 6,214,376 B1 * | 4/2001 | Gennadios ............... 424/451 |
| 6,272,366 B1 | 8/2001 | Vining |
| 2002/0081332 A1 | 6/2002 | Rampal et al. |
| 2003/0161809 A1 * | 8/2003 | Houston et al. ............ 424/85.2 |

FOREIGN PATENT DOCUMENTS

| | | | |
|---|---|---|---|
| JP | 2000232854 | * | 8/2000 |
| WO | 98/33394 | * | 8/1998 |
| WO | WO 98/52547 | * | 11/1998 |

OTHER PUBLICATIONS

Ogawa, Food Hydrocolloids, 1993, vol. 7, No. 5, pp. 397-405.*
Ogawa, Process in Colloid & Polymer Science, 1999, vol. 114 (Physical Chemistry and Industrial Application of Gellan Gum), pp. 8-14.*
JP-2000232854, Yokoi et al (Aug. 2000), Machine Translation.*
Search Report from corresponding International Application No. PCT/US02/37385 dated May 23, 2003.

* cited by examiner

*Primary Examiner*—D. L Jones
(74) *Attorney, Agent, or Firm*—Alston & Bird LLP

(57) ABSTRACT

The present invention relates to formulations for use in medical or diagnostic procedures comprising a stabilizing agent alone or in combination with an osmotic agent. In one embodiment, the stabilizing agent is a natural hydrocolloid, preferably locust bean gum, and the osmotic agent is a sugar-based compound, preferably mannitol. The present invention also relates to formulations and methods for distending an anatomic segment. The present invention further relates to formulations and methods for delineating an anatomic segment on a diagnostic image, for example. The formulations of the present invention are especially suitable for use with diagnostic imaging procedures including, but not limited to magnetic resonance imaging (MR), computer assisted tomography (CT), and CT-PET (Position emission tomography), as well as other medical and therapeutic uses.

29 Claims, 14 Drawing Sheets

FORMULATIONS FOR USE IN MEDICAL AND DIAGNOSTIC PROCEDURES

CROSS REFERENCE TO RELATED APPLICATIONS

This application claims priority from U.S. Provisional Application No. 60/332,074, filed Nov. 21, 2001, which is incorporated herein by reference in its entirety.

FIELD OF THE INVENTION

The present invention relates to formulations for use in a medical or diagnostic procedure such as diagnostic imaging or surgery, or for therapeutic use.

BACKGROUND OF THE INVENTION

Contrast agents are useful in diagnostic imaging because they make it possible to determine the location, size and conformation of organs or other structures of the body in the context of their surrounding tissues. Cells which make up the tissues of soft non-bony anatomic segments are comprised primarily of water, even among parts that differ markedly in shape and structure such as the liver, pancreas and intestine.

Diagnostic imaging techniques can detect and map variances in the composition of a target object. These imaging techniques can therefore be used to differentiate between normal tissue and tumors, lesions, or blockages, for example. Small tumors and overlapping tissues, however, are difficult to distinguish. In the diagnosis of disorders of the gastrointestinal (GI) tract, for example, blockage or abnormalities in the conformation of loops of intestine lying one on the other are difficult to identify unless the section of the GI tract is filled with a contrast agent that enables definition of volumes and delineation of boundaries.

In conventional radiographic diagnostic imaging procedure, a beam of X-rays passes through a target object and exposes an underlying photographic film. The developed film then provides an image of the radiodensity pattern of the object. Less radiodense areas produce a greater blackening of the film; more radiodense, bony tissues produce a lighter image. Effective contrast agents for X-ray may be either less radiodense than body tissues or more radiodense. The less radiodense agents include air and other gases; an example of a more radiodense contrast material is a barium sulfate suspension.

Computed tomography (CT) is superior to conventional radiography in its ability to image, with extremely high resolution, a succession of thin sections of an object at specific points, lines or planes along the X, Y, or Z axis of the target object. However, because this procedure is also based on the detection of differences in radiodensity, requirements for contrast agents in CT are essentially identical with those for conventional radiography.

Magnetic resonance imaging (MR) systems for body imaging operate on a different physical principle. Generally, MR relies on the atomic properties (nuclear resonance) of protons in tissues when they are scanned with radio frequency radiation. The protons in the tissue, which resonate at slightly different frequencies, produce a signal that a computer uses to tell one tissue from another. MR provides detailed three-dimensional soft tissue images.

Imaging methods used to obtain information about function related structure include single photon emission computerized tomography (SPECT) and positron emission tomography (PET). SPECT uses a molecule normally found in the body in which one of the atoms is replaced by a radioactive atom. The radioactive molecule, which is chosen for its ability to interact with specific tissues, is called a tracer. The tracer emits photons that can be detected as the tissue is scanned at various angles. A computer reconstructs a 3-dimensional color tracer image. PET uses radioactive biologically active tracers to produce 3-D color images with a greater sensitivity than with SPECT. PET can be used in combination with CT to create a complimentary imaging effect. This imaging technique is called CT-PET.

Diagnostic imaging of the region of the GI tract is particularly difficult because it contains anatomic segments which have higher water content than other parts of the body, and also the anatomic segments are in close proximity or overlay one another. Thus, the success of GI tract imaging is predicated upon adequate intestinal distension with a luminal contrast agent.

One conventional technique for providing distension is administering a methylcellulose-water solution via a fluoroscopically placed nasoduodenal tube. Image sets are collected following rapid filling of the entire small bowel, for example. While the technique provides good image quality, many patients perceive the duodenal intubation as traumatizing, thereby tainting the non-invasive character inherent to imaging.

Other conventional contrast agents include $CO_2$ gas, which is known to have an enhancing effect, particularly in the GI tract. Also, GI imaging has been enhanced with mineral oil. It is also known to use fluorocarbons, including brominated perfluorocarbons, as a contrast enhancement medium in radiological imaging as shown in U.S. Pat. No. 3,975,512 to Long. Other contrast agents used with MR include, for example, barium and clay-based media taken by the patient prior to the diagnostic imaging procedure.

An early proposal suggested that air be directly introduced into the desired location in the intestine via intubation (see, e.g., U.S. Pat. No. 4,074,709) as a means of enhancing the GI tract for imaging. Subsequently, in conjunction with the use of barium and clay-based contrast media, it was proposed that one might expand or distend the part under examination by directly introducing powder, granules or tablets into the medium which would then release carbon dioxide into the intestine. Maintaining the gas in aqueous medium proved to be a problem, however, and often required the use of a pressurized vessel to dissolve the gas in the contrast solution (see, e.g., U.S. Pat. No. 4,215,103).

A problem with the conventional contrast media described above is that they do not enable small lesions, such as shallow ulcers, and flat or surface ulcers, to be accurately detected in an anatomic segment. Another problem with conventional contrast media is that they may cause the patient great discomfort. For example, administering the contrast media via intubation is invasive and possibly dangerous if distension of the anatomic segment is not strictly controlled. Also, conventional contrast media can cause patient side effects, such as diarrhea, which not only cause patient discomfort, but may also interrupt and/or delay a medical or diagnostic procedure. Further, traditional contrast media are generally unpalatable when administered orally. For example, patients often describe fluorocarbon media as having a "slick" mouth-feel. Thus, there is a need or a non-invasive, palatable contrast agent with reduced side-effects to the patient. Further, this contrast agent must sufficiently distend the anatomic segment such that sufficient delineation of the anatomic segment is achieved on the diagnostic image. The image must be sufficient to detect tumors, small lesions, shallow ulcers and flat or surface ulcers.

Accordingly, the present invention is directed to non-invasive, palatable formulations for use in a medical or diagnostic procedure, especially for diagnostic imaging of an anatomic segment such as the GI tract. Additionally, the formulations disclosed herein have reduced patient side-effects compared to conventional contrast media.

SUMMARY OF THE INVENTION

The present invention is directed, in part, to formulations for use in a medical or diagnostic procedure. Specifically, the formulations comprise a stabilizing agent, alone or in combination with an osmotic agent. The invention also relates to methods for performing a medical or diagnostic procedure comprising administering the formulations disclosed herein.

The present invention further relates to formulations for use in imaging an anatomic segment of an individual comprising a stabilizing agent, alone or in combination with an osmotic agent.

The present invention also relates to formulations and methods for delineating an anatomic segment of an individual on a diagnostic image. Additionally, the present invention relates to formulations and methods for distending an anatomic segment of a patient, such as the gastrointestinal tract.

Additionally, the present invention relates to methods of imaging an anatomic segment comprising the step of administering to the patient therapeutically or diagnostically effective amount of the formulation of the present invention, and then imaging the anatomic segment using a diagnostic imaging technique or performing a medical procedure on the anatomic segment.

The invention also relates to methods for diagnosing diseases. The present invention may be used to diagnose diseases including, but not limited to, Inflammatory Bowel Disease, Crohn's Disease, ulcerative colitis, Irritable Bowel Syndrome, cancer of the small bowel, anal cancer, colon cancer, liver cancer, pancreatic cancer, abscesses, ulcers, and disorders of the spleen, liver, lymph nodes and vasculature.

In an alternative embodiment, the present invention relates to formulations and methods for performing gastrointestinal viewing or imaging procedures, including but not limited to, endoscopy, x-ray imaging, virtual imaging, which includes any technique of using computer software to view the inside of the gastrointesnal tract.

In another alternative embodiment, the present invention relates to formulations and methods for performing a colorectal examination.

Finally, the present invention relates to formulations and methods for therapeutic relief comprising the formulations of the present invention.

DETAILED DESCRIPTION OF THE INVENTION

Figure 1:
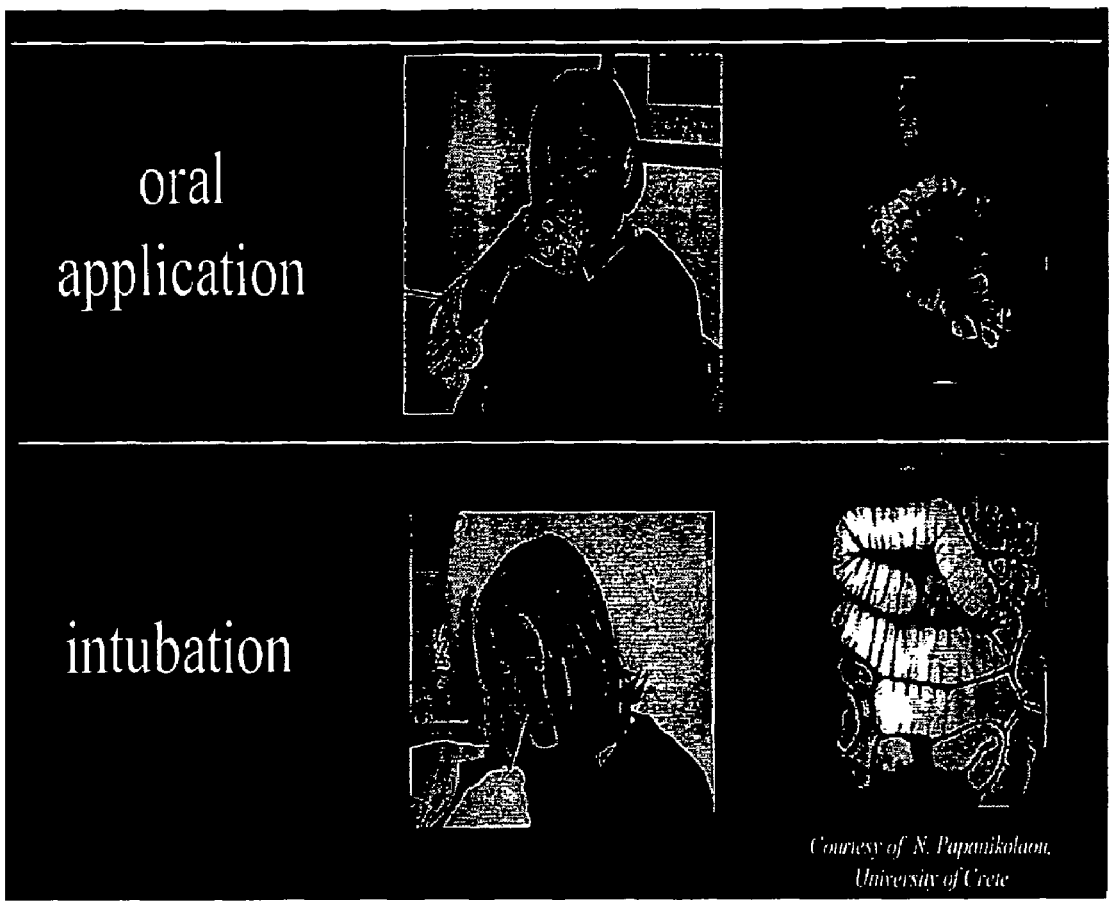
FIG. 1 shows individual's receiving conventional oral and intubation contrast agents, together with corresponding MRI images of the small intestine.

The present invention is directed to formulations suitable for use in a medical or diagnostic procedure such as diagnostic imaging. Diagnostic imaging techniques suitable for use herein include, but are not limited to, X-ray imaging, MR, CT, US, optical imaging, SPECT, PET, and flat-panel imaging. A combination of CT and PET imaging, namely, CT-PET is also suitable for use with the present invention. Preferably, the diagnostic imaging technique used herein is MR, CT or CT-PET.

More particularly, the present invention relates to contrast formulations for diagnostic imaging comprising a stabilizing agent alone or in combination with an osmotic agent. A stabilizing agent may include compounds that modify the viscosity of a substance, including fluids, semi-fluids or solid. It is believed that stabilizing agents are useful in medical or diagnostic procedures because they cause suitable amounts of fluid to be retained in an anatomic segment of interest. For example, if a diagnostic image of the small intestine is desired, administering to the patient the formulation of the present invention would cause sufficient fluid to be retained in the small intestine such that the small intestine is properly distended for diagnostic imaging. Properly distending an anatomic segment for diagnostic imaging is necessary to sufficiently delineating the anatomic segment on the diagnostic image. For example, if the small intestine is properly distended and then imaged, then the small intestine appears sufficiently delineated on the diagnostic image, thereby enabling a doctor to identify any potential problems and/or abnormalities in the patient's small intestine.

The present contrast formulations are useful in diagnostic imaging of any anatomic segment of the body. The present invention is especially suited for use in diagnostic imaging of anatomic segments including, but not limited to, the stomach and GI tract, including the duodenum, jejunum, ileum, appendix and colon such as the large intestine, cecum, ascending bowel, transverse colon, splenic flexure, descending colon, sigmoid and rectum. Additionally, the present invention is particularly suited for imaging the pancreas, gall bladder, appendix, spleen, liver, lymph nodes, vasculature and the like. This is because when the GI tract, for example, is properly distended and therefore sufficiently delineated on a diagnostic image, the doctor is able to see more clearly in the diagnostic image obtained any surrounding organs, such as the pancreas, for example.

Stabilizing agents suitable for use herein may include, but are not limited to, natural hydrocolloids, or any other similar compound that appropriately modifies the viscosity of a substance (e.g., fluid, semi-fluid and solid) in an anatomic segment in order to prepare for a medical or diagnostic procedure. In many instances, it is desirable to increase the viscosity of a substance in the anatomic segment to obtain suitable distention of the anatomic segment. However, it may be desirable in some instances to decrease the viscosity of a substance in the patient's anatomic segment, for example, if the viscosity of the substance is such that it is intolerable to the patient or insufficient volume of contrast formulation can be administered to the patient. Further, if the present formulations are administered via intubation, then less viscosity may be desired or needed than if the present formulations are administered orally, for example.

Natural hydrocolloids suitable for use in the present formulations include, but are not limited to, (1) natural seaweed extracts such as carrageenan, alginates, agar, agarose, fucellan and xanthan gum; (2) natural seed gums such as guar gum, locust bean gum, tara gum, tamarind gum and psillium gum; (3) natural plant exudates acacia, tragacanth, karaya and ghatti gums; and, (4) natural fruit extracts such as low and high methoxyl pectins.

In a preferred embodiment, the stabilizing agent is a natural seed gum, and, even more preferably, locust bean gum. The chemical structure of locust bean gum is:

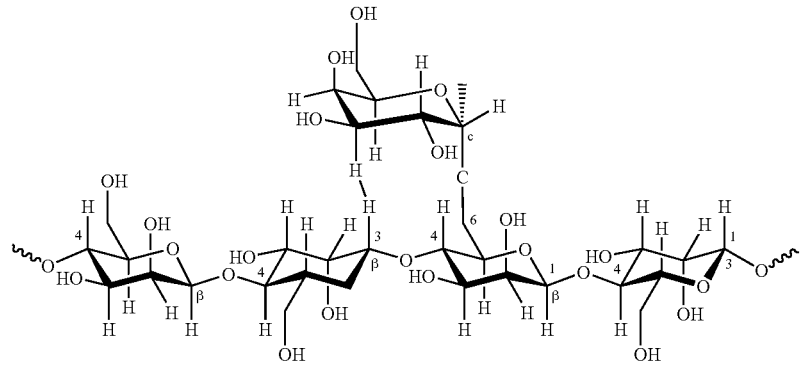

In one embodiment, the present invention relates to a formulation comprising about 0.005% to about 70% by weight of a stabilizing agent in an aqueous solution, or about 0.05% to about 25% of a stabilizing agent, or about 0.005% to about 0.1%, or about 0.1% to about 10% of a stabilizing agent. As used herein, percentages of ingredient represent by weight percentages, unless otherwise stated. In another embodiment, the present invention relates to a formulation comprising about 0.1%, 0.2%, 0.3%, 0.4%, 0.5%, 0.6%, 0.7%, 0.8%, 0.9% or 1% by weight of a stabilizing agent in an aqueous solution. In another embodiment, the present invention relates to a formulation comprising 1%, 2%, 3%, 4%, 5%, 6%, 7%, 8%, 9% or 10% in an aqueous solution. Preferably, the contrast agent is a formulation comprising about 0.25% to about 0.3% by weight locust bean gum in an aqueous solution. Other stabilizing agents may include cellulose, gelatin or any other similar compound that appropriately modifies the viscosity of a substance (e.g. fluid semi-fluid or solid) in an anatomic segment.

The present invention also relates to a formulation comprising a stabilizing agent in combination with an osmotic agent in an aqueous solution. Osmotic agents suitable for use herein include any compound that facilitates the transfer of fluid from the body into an anatomic segment and/or facilitates the inhibition of fluid re-absorption in the anatomic segment by the body. It has been discovered that, when used in combination, the stabilizing agent (e.g. natural hydrocolloids) and the osmotic agent (e.g. sugar-based compound) act synergistically to form an improved formulation for use in a medical diagnostic procedure such as diagnostic imaging. It is believed that the osmotic agent facilitates the transfer of suitable amounts of fluid into an anatomic segment of interest and that the stabilizing agent and osmotic agent cause sufficient amounts of fluid to be retained in the anatomic segment of interest. Thus, the anatomic segment is sufficiently expanded or distended for diagnostic imaging, such that when the anatomic segment is imaged, for example, then the anatomic segment appears sufficiently delineated on the diagnostic image obtained.

Osmotic agents suitable for use in the present invention include, but are not limited to, sugar-based compounds. Sugar-based compounds for use herein include, but are not limited to, monosaccharide, disaccharide and polysaccharides including sucrose, glucose, fructose, mannitol, mannose, galactose, aldohexose, altrose, talose, sorbitol, xylitol, lactose, nonionic seed polysaccharide, straight chain mannan grouping with branching on every mannose by one galactose unit, Beta-D-man, alpha-D-gal, D-glcA, D-galA, L-gul, beta-D-man, alpha-D-gal (4:1), D-glucuronic acid, D-galacturonic acid, and L-glucuronic acid. The chemical structure of a suitable polysaccharide is shown below. Preferably, the osmotic agent is mannitol.

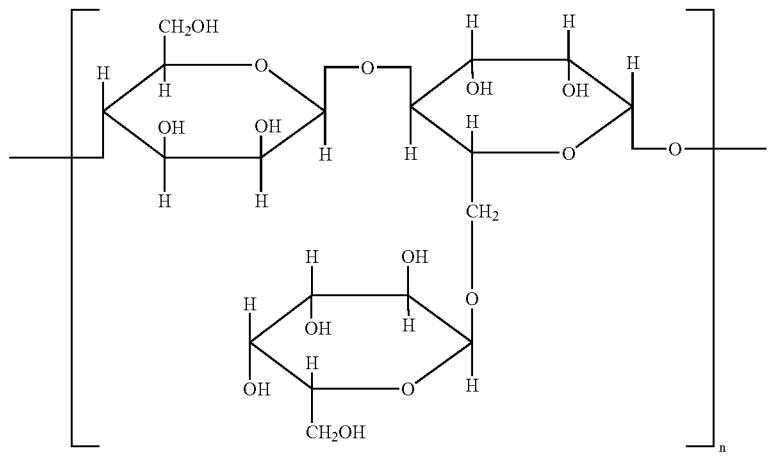

The formulation of the present invention may comprise about 0.005% to about 70% by weight of an osmotic agent, or about 0.10% to about 45% by weight of an osmotic agent, or about 1%, 2%, 3%, 4%, 5%, 6%, 7%, 8%, 9%, or 10% by weight of an osmotic agent, or about 11% to about 20% by weight of an osmotic agent. In one embodiment, the formulation comprises about 2% to about 4% by weight of an osmotic agent, preferably a polysaccharide, or even more preferably about 3% of mannitol in an aqueous solution. In an embodiment, the present formulation comprises about 0.1% to about 0.5% by weight locust bean gum and about 1% to about 8% by weight of mannitol in an aqueous solution, or preferably about 0.25% locust bean gum and about 3% mannitol in an aqueous solution.

The formulations of the present invention are also suitable for preparing an individual for a medical activity such as surgery or biopsy, or for use simultaneously with such medical activity. For example, the formulations disclosed herein can be used simultaneously with a medical procedure to compliment or enhance the effectiveness of such a procedure. In one embodiment, the formulations of the present invention are administered to an individual prior to the individual undergoing a biopsy of the bowel, such that the bowel is sufficiently stabilized during performance of the biopsy. In another embodiment, the formulations of the present invention are used to stabilize the GI tract of an individual in order to obtain a diagnostic image of the vasculature system or the lymph nodes or other anatomical segment.

The present invention further relates to formulations for delineating the lumen or wall of an anatomic segment on a diagnostic image, the diagnostic image being a two- or three-dimensional image of the anatomic segment. The formulations for delineating comprising, in an aqueous solution, a stabilizing agent alone or in combination with an osmotic agent. In one embodiment, the composition comprises about 0.005% to about 70% by weight of a stabilizing agent in an aqueous solution, or about 0.05% to about 5% of a stabilizing agent, or about 0.1%, 0.2%, 0.3%, 0.4%, 0.5%, 0.6%, 0.7%, 0.8%, 0.9% or about 1% by weight of a stabilizing agent in an aqueous solution. In a preferred embodiment, the formulation for delineating the lumen of an anatomic segment of an individual on a diagnostic image comprises about 0.1% to about 0.3% by weight locust bean gum in aqueous solution, or about 0.25% locust bean gum in an aqueous solution.

Further, the formulations of the present invention for delineating the lumen of an anatomic segment on a diagnostic image may comprise about 0.005% to about 70% of an osmotic agent, or about 1% to about 35% of an osmotic agent, or about 1.5%, 2%, 2.5%, 3%, 3.5%, 4%, 4.5% or 5% by weight of an osmotic agent. Preferably, the formulation comprises about 2% to about 5% by weight mannitol, or about 3% mannitol. In a preferred embodiment, the formulation comprises about 0.3% locust bean gum and about 3.0% mannitol in an aqueous solution.

The present invention also relates to formulations for distending an anatomic segment of an individual for a medical or diagnostic procedure. The formulations comprising, in an aqueous solution, a stabilizing agent alone or in combination with an osmotic agent. In one embodiment, the formulation comprises about 0.005% to about 70% by weight of a stabilizing agent, or about 0.05% to about 25% of a stabilizing agent, or about 0.1% to about 8% of a stabilizing agent in an aqueous solution. Further, the formulation may comprise about 0.005% to about 70% of an osmotic agent, or preferably about 0.1% to about 10% of an osmotic agent. In one embodiment, the formulation for distending an anatomic segment for a medical procedure or diagnostic image comprises about 0.1% to about 0.5% locust bean gum and about 1% to about 10% mannitol in an aqueous solution.

The aqueous solution of the present invention may be about 10 mL to about 10 L, or about 100 mL to about 5 L, or about 200 mL, 300 mL, 400 mL, 500 mL, 600 mL, 700 mL, 800 mL, 900 mL, 1 L, 1.5 L, 2 L, 2.5 L, 3 L, 3.5 L, 4 L or 4.5 L.

In one embodiment, the formulations of the present invention are administered orally. In an alternative embodiment, the formulations of the present invention are administered via intubation.

In one embodiment, the formulation of the present invention is made from dissolving 2 grams of commercial grade locust bean gum powder in 1 liter of water. The locust bean gum-water solution is then heated until the locust bean gum powder is dissolved, at which point the solution is then sterilized. After the solution is sterilized, 25 g of commercial grade mannitol are added to the solution.

The formulations of the present invention represent an improvement over conventional contrast agents or formulations for distending or delineating an anatomical segment. For example, a conventional technique of distending the colon is administering a methylcellulose-water solution via intubation, an invasive procedure. The present formulations, however, can be administered orally. Thus, the formulations of the present invention are non-invasive, and also maintain the integrity of diagnostic imaging as a non-invasive technique. Also, when administered orally, the present formulations increase patient comfort and compliance as compared to conventional contrast agents.

Further, the formulations of the present invention represent an improvement over conventional contrast agents in that may be administered orally with relative ease and comfort to the patient. Traditional fluorocarbon contrast media have a "slick" mouth-feel and are not soluble in fruit drinks. In contrast, the present formulations may be formulated so that they do not have a slick-mouth feel when administered orally and can be administered in combination with artificial flavorings.

Further, it has been discovered that the formulations disclosed herein have the unexpected benefit of reducing incidents of diarrhea among patients. For example, when mannitol alone is administered as a contrast agent, approximately 99% of patients experience diarrhea, sometimes in severe form. As a result, the patient's health and/or hydration may be affected, and the exam may be compromised. The present formulations, however, were found to significantly reduce incidents or diarrhea among patients. It is believed that this is due to the thickening properties of the stabilizing agent. Accordingly, due to the patient not having to use the bathroom during the procedure, for example, the medical or diagnostic procedure can be performed with less patient discomfort and with less interference. Additionally, patient compliance with the medical or diagnostic procedure is increased due to decreased complications with the procedure.

Another benefit of the formulations herein is that they provide sufficient distension of the anatomic segment such that it appears sufficiently delineated on a diagnostic image. This represents an improvement over the use of conventional contrast agents. For example, a conventional imaging contrast agent is water administered to the patient prior to scanning in order to distend the patient's bowel. One problem with this method is the rapid re-absorption of the water by the body, which diminishes distension of the anatomic segment over time. Such reduction may occur prior to the medical or diagnostic procedure such that the window of opportunity for successfully completing the procedure is small. Also, with respect to a diagnostic imaging procedure, for example, because the imaging procedure can last for hours, it is possible that the distention level of the anatomic segment being imaged will decrease significantly over the length of the procedure, such that there is compromised signal homogeneity. The present invention overcomes the problem of rapid re-absorption because the properties of the stabilizing agent, i.e., its ability to act as a thickener and to increase the viscosity of a fluid, cause suitable amounts of fluid to be retained in the anatomic segment over a sufficient period of time, thereby increasing the window of opportunity for obtaining a meaningful diagnostic image and maintaining signal homogeneity during the length of the scanning procedure so that a better diagnostic image is obtained. Accordingly, the need for repeated scans is reduced or eliminated when the present formulations are used as contrast agents.

The present invention also relates to an improved method for diagnostic imaging of an anatomic segment of an individual comprising administering the formulations disclosed herein to a patient. Diagnostic imaging techniques suitable for use herein include, but are not limited to, X-ray imaging, MR, CT, US, optical imaging, SPECT, PET, CT-PET and flat-panel imaging. Preferably, the diagnostic imaging technique used herein is MR, CT or CT-PET.

In one embodiment, the present invention relates to a method of imaging the small intestine of an individual comprising administering to the individual the formulations disclosed herein and using MR, CT or CT-PET to obtain a visible image of the small intestine. Other anatomic segments suitable for use herein include, but are not limited to, the stomach and GI tract, including the duodenum, jejunum, ileum, appendix, colon, large intestine, cecum, ascending bowel, transverse colon, splenic flexure, descending colon, sigmoid, rectum, pancreas, gall bladder, appendix, spleen, liver, lymph nodes, vasculature and the like.

In an alternative embodiment, the present invention relates to a method of diagnosing a disease in an individual comprising administering to the patient the formulations of the present invention. In one embodiment, the method further comprises obtaining an image of the anatomic segment and using said image to diagnose said disease. In an alternative embodiment, the present invention relates to a method of diagnosing a disease in a patient comprising the steps of: (1) administering to the patient a therapeutically or diagnostically effective amount of the present formulation comprising a stabilizing agent alone or in combination with an osmotic agent, (2) obtaining an image of the anatomic segment using MR, CT or CT-PET, and (3) using said image to diagnose or assist in diagnosing a disease.

The present invention represents an improvement over conventional diagnosis using diagnostic imaging techniques due to the improved distension and delineation of the anatomic segment, which facilitates diagnosis. The present invention may be used to diagnose diseases including, but not limited to, diseases of the GI tract, ulcerations, lesions, tumors or abscesses of the GI tract or stomach, Inflammatory Bowel Disease, Crohn's Disease, ulcerative colitis, diverticulitis, Irritable Bowel Syndrome, and cancer including, but not limited to, cancer of the small bowel, anal cancer, stomach cancer, colon cancer, liver cancer and pancreatic cancer. Additionally, the present invention may be used to diagnose disorders or diseases of the lymph nodes, spleen or appendix, vasculature and the like.

The present invention further relates to an improved method for delineating an anatomic segment of an individual on a diagnostic image comprising administering the formulations disclosed herein. Preferably, the diagnostic image is a two- or three-dimensional image created using MR, CT or CT-PET.

The present invention additionally relates to an improved method for distending an anatomic segment of an individual. The method of the present invention is an improvement over conventional techniques used to distend anatomic segments for medical or diagnostic procedures because re-absorption of fluid by the body is delayed or minimized, such that the anatomic segment is more suitably distended and/or distension is maintained for a longer period of time. The method of the present invention is further an improvement over conventional diagnostic imaging methods due to improved signal homogeneity.

The present invention also relates to formulations for distending an anatomic segment of an individual for therapeutic purposes comprising a stabilizing agent alone or in combination with an osmotic agent. The present invention also relates to an improved method for distending the anatomic segment of a patient for therapeutic purposes comprising administering a patient in need thereof the formulations of the present invention. For example, the present formulations may be administered to therapeutically treat an individual suffering from ulcerations, lesions, tumors or abscesses of the GI tract, GI tract bleeding, Inflammatory Bowel Disease, Crohn's Disease, ulcerative colitis or Irritable Bowel Syndrome.

The present invention additionally relates to an improved method for performing a medical or diagnostic procedure on an individual comprising: (1) administering to the patient a gastric-emptying substance prior to the conducting step to increase emptying of the stomach contents of the patient, (2) administering to the patient a formulation comprising, in an aqueous solution, a stabilizing agent alone or in combination with an osmotic agent, and (3) conducting said medical or diagnostic procedure. The formulation comprising about 0.005% to about 70% by weight of a stabilizing agent alone or in combination with about 0.005% to about 70% of an osmotic agent. Preferably, the stabilizing agent is locust bean gum and the osmotic agent is mannitol. Gastric-emptying substances suitable for use herein include, but are not limited to, Erythromycin, Paspertin, serotonin agonists and the like. These may be administered to the patient orally or intravenously, for example.

In an alternative embodiment, the present invention relates to a method for imaging an anatomic segment of an individual comprising the steps of: (1) administering to the patient about 10 mg to about 100 mg of Erythromycin to increase emptying of the patient's stomach contents approximately 1 hour prior to the scanning step; (2) administering to the patient an aqueous solution comprising about 0.01% to about 25% of locust bean gum and about 1.0% to about 50.0% of mannitol in a 1.5 liter aqueous solution approximately 1 hour prior to the scanning step; and (3) scanning the patient using MR, CT or CT-PET to obtain a visible image of the small intestine of the patient.

In one embodiment, the gastric-emptying substance is administered about 10 minutes to about 8 hours prior to the imaging or scanning procedure, or immediately prior to the procedure. In another embodiment, the aqueous solution is administered about 10 minutes to about 8 hours prior to the scanning procedure, or about immediately prior to the scanning procedure, or about 180 minutes, 120 minutes, 90 minutes, 60 minutes or about 30 minutes prior to the scanning procedure.

The aqueous solution provided may be about 50 mL to about 5 L, or about 100 mL to about 1.5L, or about 200 mL, 300 mL, 400 niL, 500 niL, 600 mL, 700 mL, 800 mL, 900 mL, 1 L, 1.5 L, 2 L, 2.5 L or about 3 L. The aqueous solution may be administered in single dosage, or may be divided into multiple dosages. For example, if the aqueous solution is 2 L, then the patient may consume 1 L about 2 hours prior to the procedure, and the remaining 1 L about 1 hour prior to the procedure.

The present invention also relates to a formulation and improved method for performing a colo-rectal examination, the formulation comprising a stabilizing agent, alone or in combination with an osmotic agent, in an aqueous solution. Preferably, the formulation comprises about 0.01% to about 30% locust bean gum and about 0.1% to about 30% mannitol in an aqueous solution. Such method comprising administering to a patient the formulations of the present invention rectally.

EXAMPLES

This invention may be further understood by a consideration of the following examples which are intended to be purely exemplary of the use of the invention.

Example 1

Ten healthy volunteers with no history of gastrointestinal disorder underwent MR imaging following an eight hour fast. The examination was repeated on four different days using different osmotic substances in a randomized order: water, water spiked with mannitol (2.5%), Metamucil (0.7%) or locust bean gum (0.2%). Concentrations of the additives were chosen to avoid side-effects such as diarrhea.

Forty-five minutes prior to the examination, 50 mg of Erythromycin was applied intravenously to increase gastric emptying and the volunteers started ingesting the respective contrast substance. Coronal 2D measurements were performed in the prone patient position with a TRUFISP sequence (TR/TE/flip 3.2/1.6/70°) using 1.5 T scanner (Sonata, Siemens). The acquisition time amounted to 16 sec. Small bowel filling was quantified in two different ways: (1) determination of small bowel fluid by automatically measuring all pixels meeting the signal intensity of water, and (2) assessment of small bowel distension by manual measurement of 15 small bowel diameters and calculating an average value.

Six healthy volunteers underwent MR imaging following an eight-hour fast. The examination was repeated on five different days using different osmotic substances in a randomized order: water, water spiked with mannitol (2.5%), Metamucil (0.7%), locust bean gum (LBG, 0.2%) or the combination of mannitol (2.5%) and LBG (0.2%). 45 minutes prior to the examination, the volunteers started ingesting the respective contrast substance. Coronal 2D measurements were performed in the prone patient position with a TRUFISP sequence (TR/TE/flip 3.2/1.6/70°) using a 1.5 T scanner (Sonata, Siemens). The acquisition time amounted to 16 sec. Small bowel filling was quantified by manual measurement of 15 small bowel diameters and calculating an average value.

Patients were given an oral application of 1500 ml of different solutions 45 min prior to MR examination. In this study acquisition of coronal TrueFisp sequences without I.V. contrast was performed. Subsequently, measurement of small bowel diameters and calculation of an average value were determined.

Table 1 shows the solutions given to the participants in the study.

TABLE 1

| Volunteer | Solution |
|---|---|
| 1-1 | B |
| 1-2 | C |
| 1-3 | F |
| 1-4 | A |
| 1-5 | D |
| 1-6 | E |
| 2-1 | A |
| 2-2 | C |
| 2-3 | B |
| 2-4 | D |
| 2-5 | E |
| 3-1 | A |
| 3-2 | E |
| 3-3 | B |
| 3-4 | C |
| 3-5 | D |
| 4-1 | A |
| 4-2 | B |
| 4-3 | C |
| 4-4 | D |
| 4-5 | E |
| 5-1 | B |
| 5-2 | C |
| 5-3 | F |
| 5-4 | A |
| 5-5 | D |
| 5-6 | E |
| 6-1 | B |
| 6-2 | C |
| 6-3 | F |
| 6-4 | D |
| 6-5 | A |
| 6-6 | E |

A: water
B: Metamucil (0.7%)
C: mannitol (2.5%)
D: locust bean gum (0.2%, orange flavor)
E: mannitol (2.5%) + locust bean gum (0.2%, orange flavor)
F: locust bean gum (0.2%, strawberry flavor)

It should be noted that volunteer 2 was excluded from evaluation due to anatomical structure of the colon. Therefore, evaluation of small bowel distension was not expressive. Solution F was only tested in three volunteers. Due to unpleasant taste, volunteers were not able to ingest the complete 1500 ml. Therefore, the results of this part of the examination were not evaluated.

FIG. 1 shows the current methods of administration of a contrast agent prior to MR imaging. Currently, patients are required to be intubated to achieve optimal small bowel interrogation. As shown in FIG. 1, oral application of a water contrast agent does not achieve acceptable or diagnostic results.

In the study, 10 volunteers were examined after an 8-hour fast. Examination was repeated on four different days. On day 1, the volunteers were administered water prior to examination. On day 2, the volunteers were administered water and mannitol (2.5%) prior to examination. On day 3, the volunteers were administered water and Metamucil (0.7%) prior to examination. On day 4, the volunteers were administered water and locust bean gum (0.2%) prior to examination. The solutions provided in 1.5 liter solution, and were ingested approximately 45 minutes prior to MR examination. Examination was performed in the prone position using a 1/5T Scanner (Sonata, Siemens)—TrueFISP.

Figure 2:
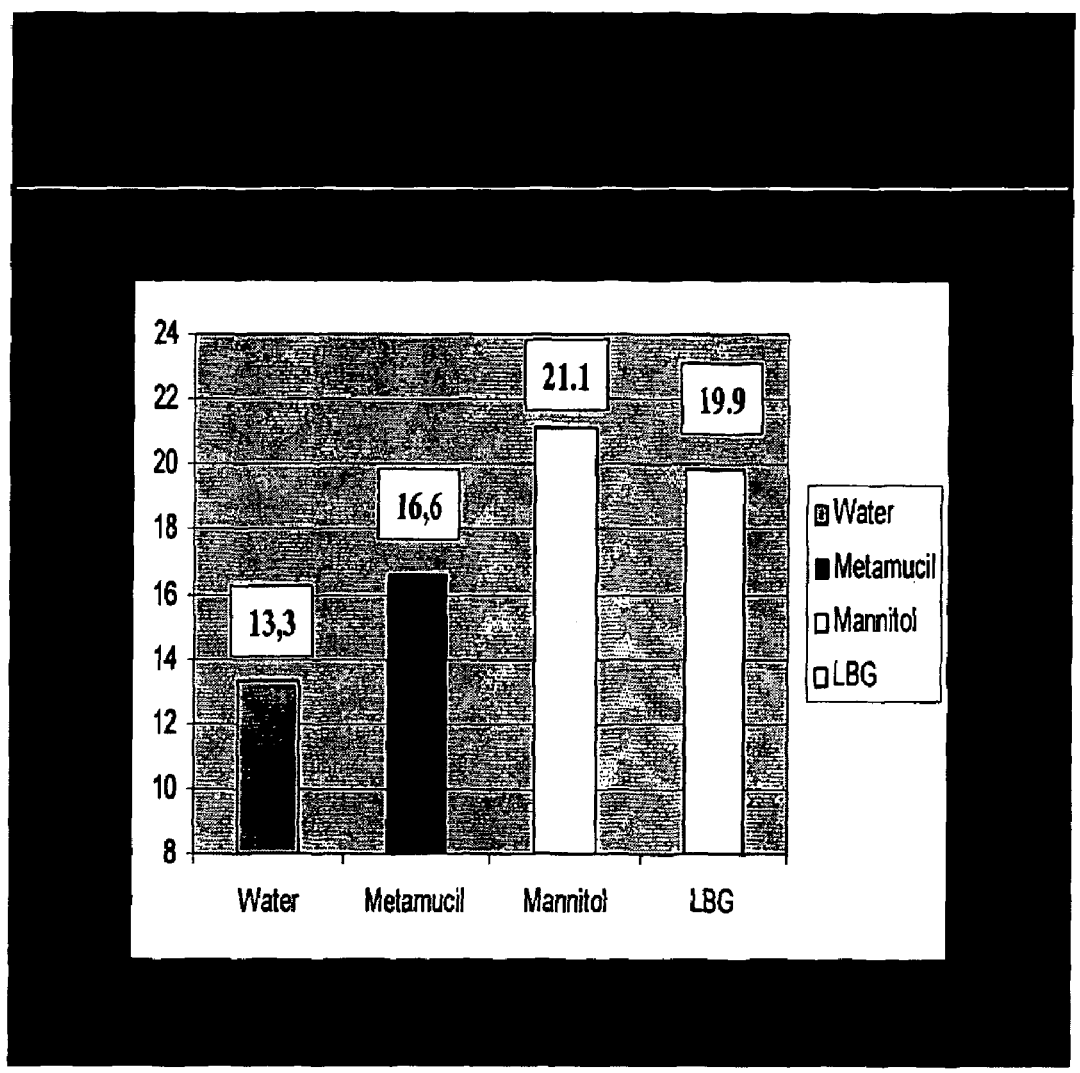
FIG. 2 shows the overall mean average of the bowel lumen diameter of 10 study volunteers.
Figure 3:
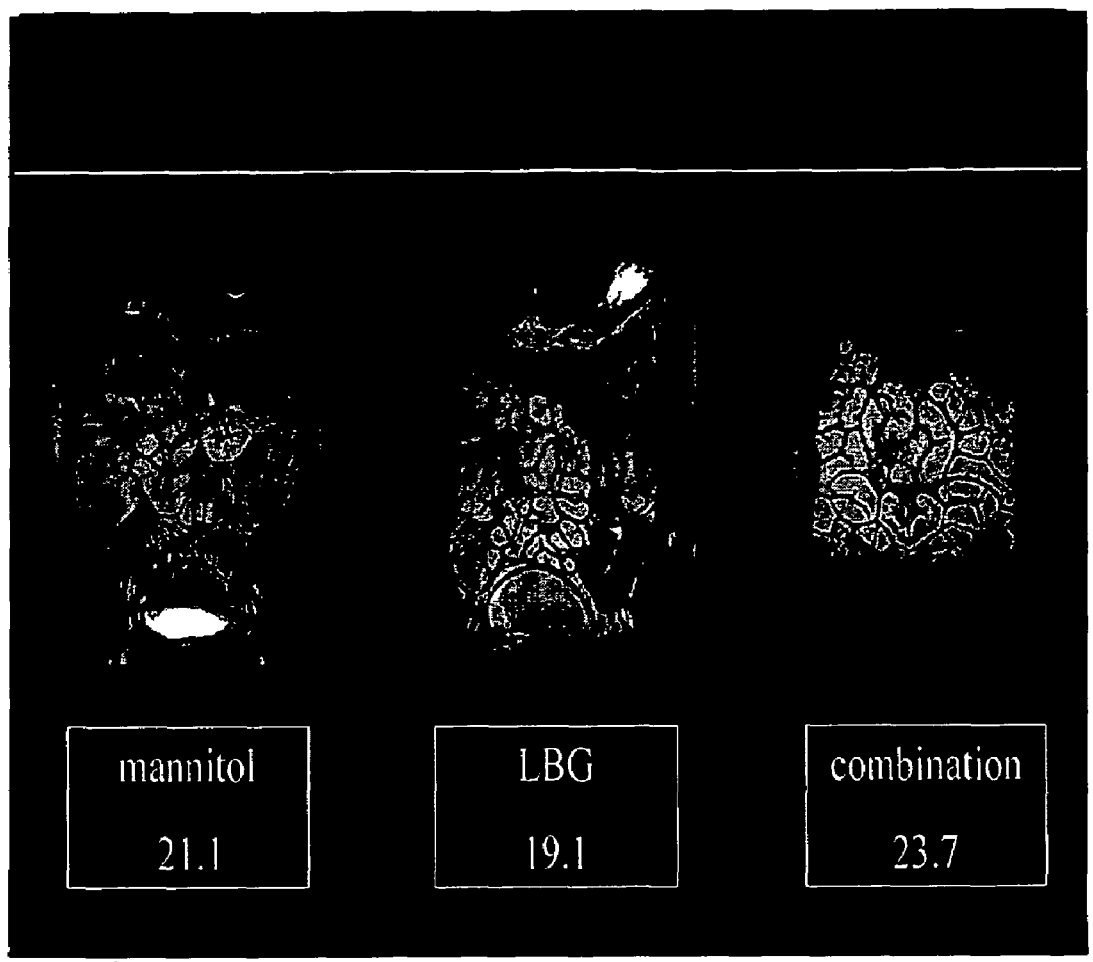
FIG. 3 is a series of images of the abdomen of an individual administered, on separate occasions, an aqueous solution comprising mannitol or locust bean gum or a combination of both compounds.

FIG. 2 shows the overall mean average of the bowel lumen diameter of the 10 patients in the study. FIG. 3 is a series of images of the abdomen of a patient that was administered, on separate occasions, an aqueous solution comprising mannitol or locust bean gum or a combination of both compounds. FIG.

3 also shows that by combining the distention and transient component of mannitol with the uniformity and consistency of the distention properties of the locust bean gum, optimal diagnostic results were achieved.

Figure 4:
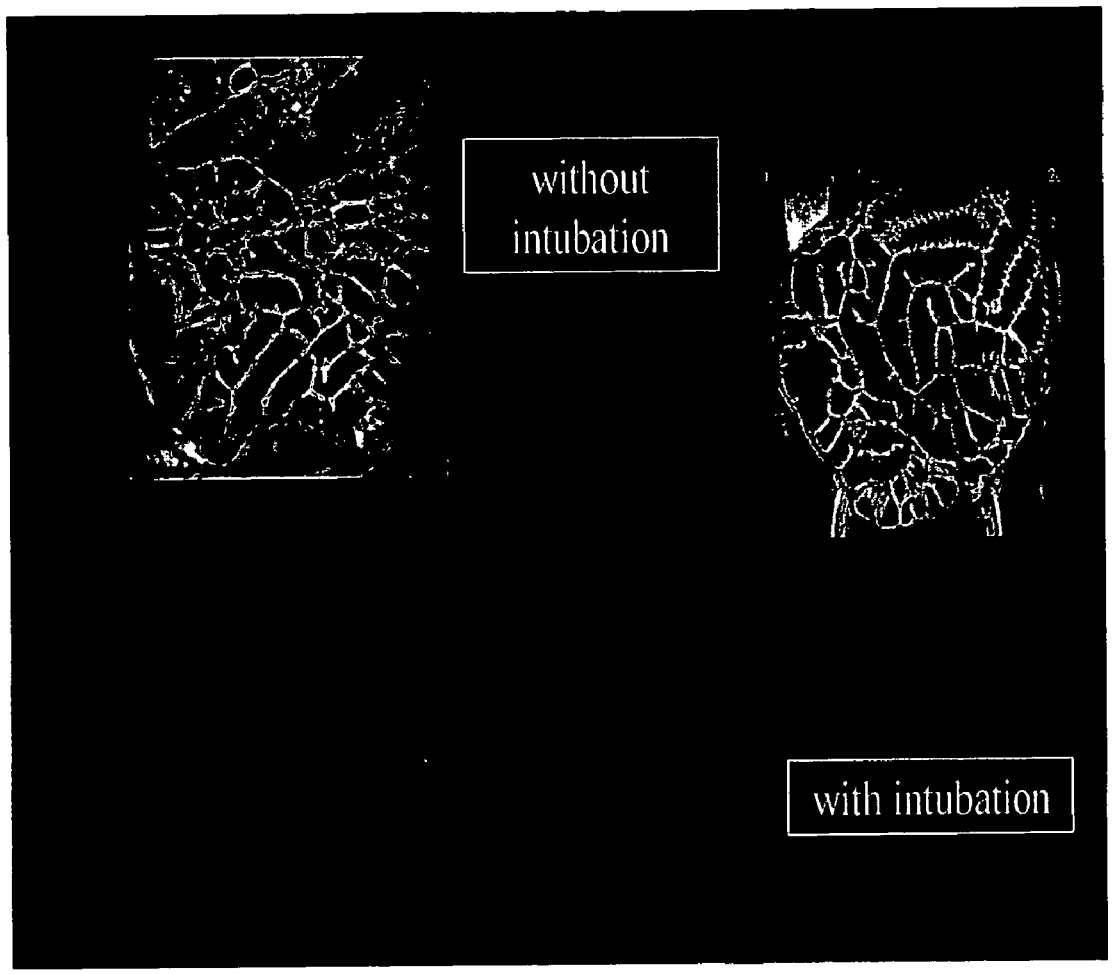
FIGS. 4 and 5 show the small intestine evaluated using locust bean gum-mannitol combination and comparing that to a bowel evaluated by intubation.
Figure 5:
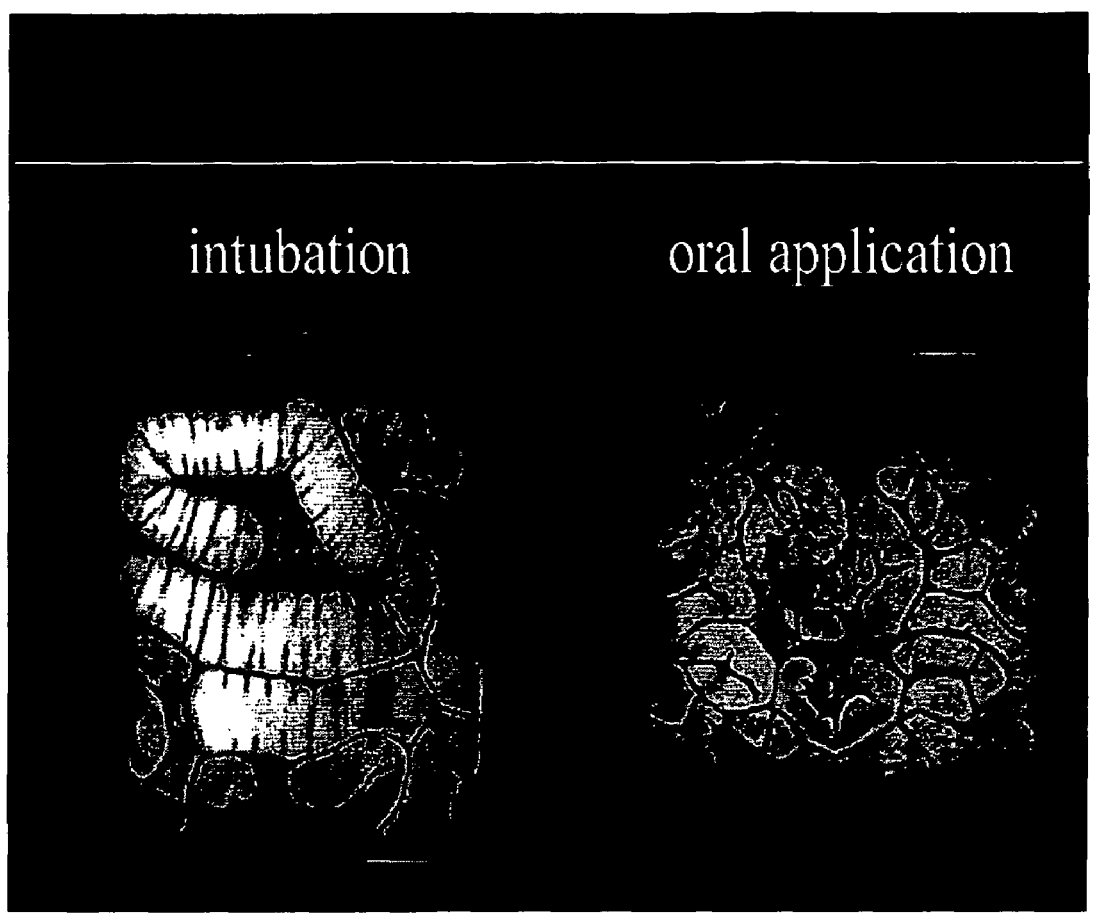

FIGS. 4 and 5 show the small bowel evaluated using locust bean gum/mannitol combination and comparing that to a bowel evaluation by intubation. These images demonstrate the performance of locust bean gum/mannitol combination taken orally is just as diagnostic as similar procedures requiring intubation.

Example 2

Figure 6:
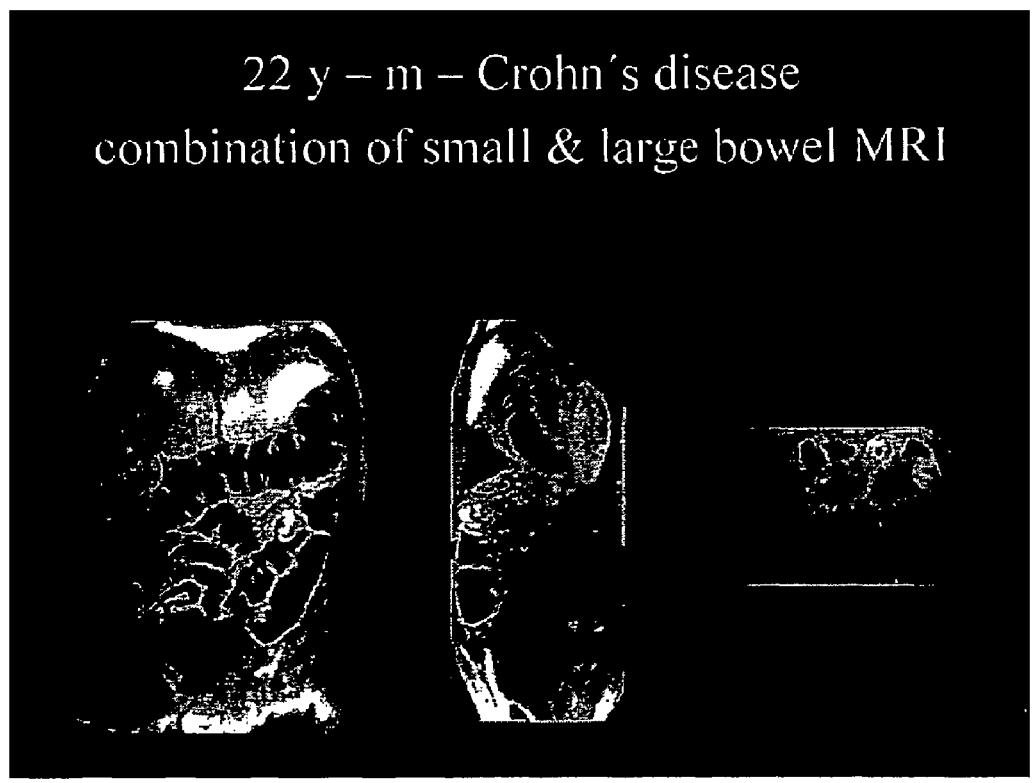
FIGS. 6-8 show gastrointestinal tracts evaluated using a locust bean gum-mannitol combination.
Figure 7:
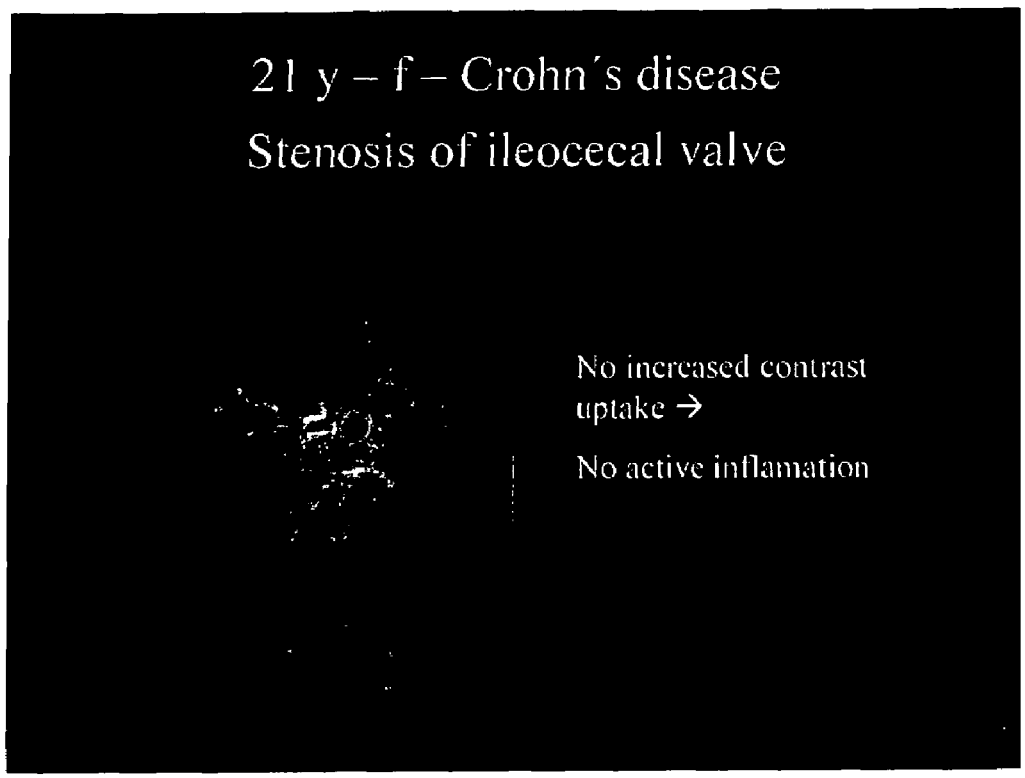
Figure 8:
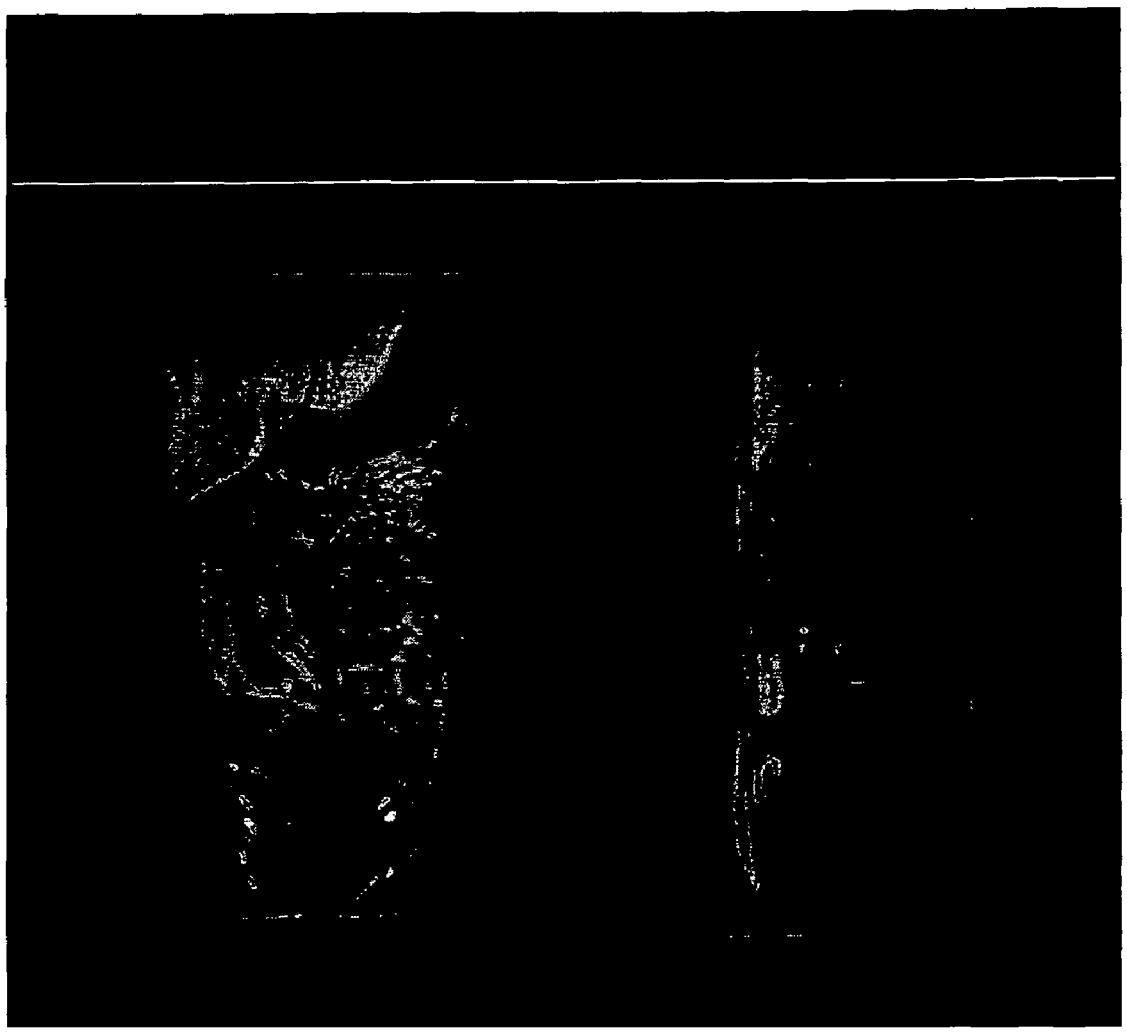

FIGS. 6-8 are patient case studies showing 18 and 21 year old females, and a 22 year old male. Each patient's gastrointestinal tract was interrogated with a locust bean gum/mannitol combination. Here, all patients were presented with and diagnosed with Crohn's disease. In each image, while areas of increased inflammation were seen on two subjects, the other subject demonstrated Crohn's disease of the ileocecal valve without active inflammation.

Example 3

Figure 9:
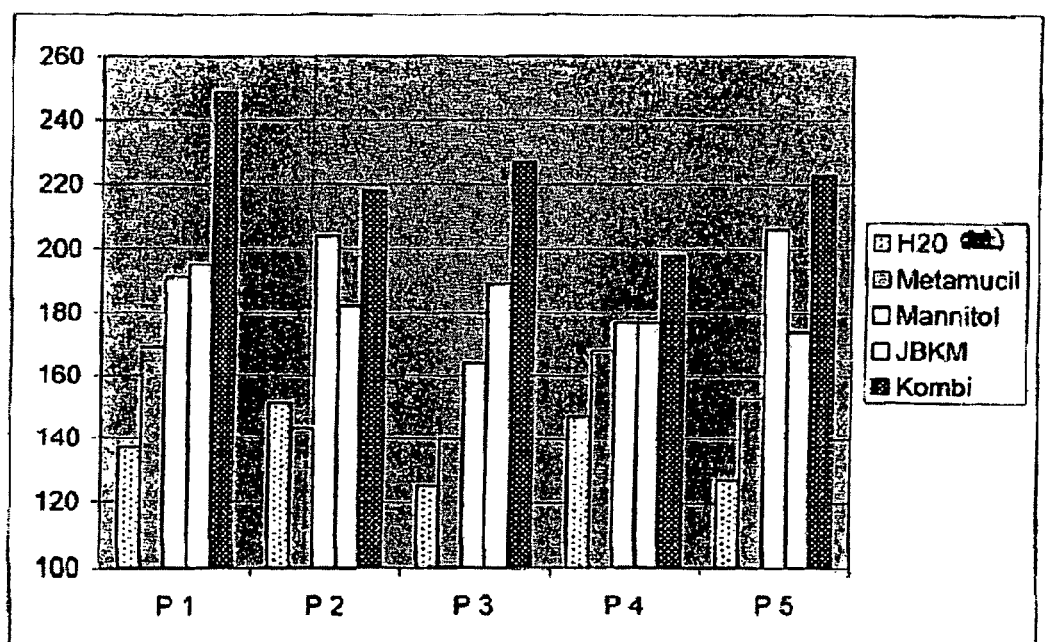
FIG. 9 shows bowels evaluated using water, Metamucil®, mannitol, locust bean gum and a locust bean gum-mannitol combination.

FIG. 9 shows the overall performance of water vs. Metamucil vs. mannitol vs. locust bean gum vs. locust bean gum/combination. This study shows that the locust bean gum combination consistently out performs the other contrast agents with respect to overall lumen distention and bowel lumen differentiation. Thus, the locust bean gum/mannitol combination eliminates the need to intubate the patient for small bowel investigation.

In sum, FIGS. 1-9 demonstrate, among other things, that the performance of the oral locust bean gum/mannitol combination is not only effective in normal patients, but also in the presence of pathologic conditions, such as Chron's disease.

Example 4

Six healthy volunteers (three female and three male; age range 21-28 years) without known contraindications to MR imaging were included in this study, which was conducted in accordance with all guidelines set forth by the approving institutional review board. Presence of gastrointestinal disease, previous abdominal surgery and symptoms of gastrointestinal disorders such as post-prandiol belching, nausea or early satiety were excluded. Each volunteer was examined on five different occasions.

Tap water, which renders the bowel lumen bright on T2- and dark on T1-weighted images, was used as a contrast agent. It was evaluated without additives as a baseline and compared to four solutions containing osmotic and/or non-osmotic additives: a 0.7% solution of Metamucil (Mucofalk®, Falk Pharma, Freiburg, Germany), a 2.5% solution of mannitol (Merck, Darmstadt, Germany), a 0.2% solution of locust bean gum (LBG) (Roeper, Hamburg, Germany) and a solution containing 2.5% mannitol and 0.2% LBG. The LBG and Metamucil concentrations were chosen as high as possible within the confines of an unproblematic ingestion regarding viscosity and flavor, while choice of the mannitol concentration was based on previous studies.

To assure homogenization of bowel activity, all exams were performed following 8 hour fasts. Prior to each exam, 1500 ml of the respective contrast solution were orally ingested over 45 minutes at a steady, evenly distributed rate. To ensure a consistent ingestion, volunteers were asked to drink 150 ml every four to five minutes. To enhance gastric emptying, 100 mg erythromycin (Abbott Pharmaceutics, Wiesbaden, Germany) were administered intravenously directly after the ingestion of the first 150 ml of the contrast solution.

MR examinations were performed on a 1.5 T system (Magnetom Sonata, Siemens Medical Systems, Erlangen, Germany) equipped with high-performance gradient systems characterized by a maximum gradient amplitude of 40 mT/m and a slew rate of 200 mT/m/msec. For signal reception a large 'flex surface coils' was used. Prior to the data acquisition neither spasmolytic agents nor paramagnetic contrast compounds were intravenously applied. Coronal 2D images were collected in the prone patient position with a T2-weighted fast imaging with steady state precession sequence (TrueFISP, TR/TE/flip 3.9/1.9/70°). Other sequence parameters included a field of view 35 cm, a slice thickness of 7 mm (25 slices) and an acquisition time of 24 seconds. Matrix size was 144×256, inter section gap amounted to 1 mm and the number of excitation was one. All 30 MR examinations were of diagnostic image quality. 1500 ml of each solution was ingested within the target time of 45 minutes.

Images were quantitatively analyzed independently by two radiologists, who were blinded to the type of oral contrast employed. On a postprocessing workstation (Virtuoso, Siemens Medical Systems, Erlangen, Germany), each radiologist measured 5 small bowel loop diameters both in the jejunum and the ileum. For the measurements bowel loops with maximal diameter were chosen. Thus 20 bowel diameters were obtained for each MR examination. Subsequent analysis was based on mean small bowel diameters and their standard deviations.

For a qualitative assessment, MR images of all 5 examinations for each volunteer were presented as hardcopies in a randomized and blinded fashion to five radiologists. They were asked to rate the images regarding bowel distention in an ascending order for each volunteer. The qualitative assessment was done by consensus.

Twenty-four hours after each MR examination, volunteers were asked by a standardized questionnaire based on a three-point scale (0=no side-effects, 1=mild side-effects, 2=severe side-effects) if either diarrhea or nausea have occurred in association with the contrast ingestion.

The effects of the analyzed oral contrast agents concerning small bowel distension were compared by a paired t-test. For the adaptation to multiple samples, a Bonferoni-correction was used. For all statistical analyses, a P values <0.01 was considered to indicate a statistically significant difference.

Figure 10:
FIG. 10 shows the bowel as imaged by steady state precession sequence imaging (TrueFISP).

The avid contrast between the bright, liquid containing small bowel lumen and the dark surrounding tissues on fast imaging with steady state precession sequence (TrueFISP) images (FIG. 10), permitted a distinct delineation between bowel wall and bowel lumen. Severe (mild) diarrhea was identified as a side effect in 2 of 6 volunteers following the ingestion of the mannitol solution. One volunteer reported mild diarrhea following the ingestion of the solution containing locust bean gum and mannitol. Nausea as a side-effect was not experienced.

Figure 11:
FIG. 11 shows images of the bowel of an individual using different contrast agents: (a) water, (b) Metamucil®, (c) locust bean gum, (d) mannitol, and (e) a locust bean gum—mannitol combination.
Figure 11:
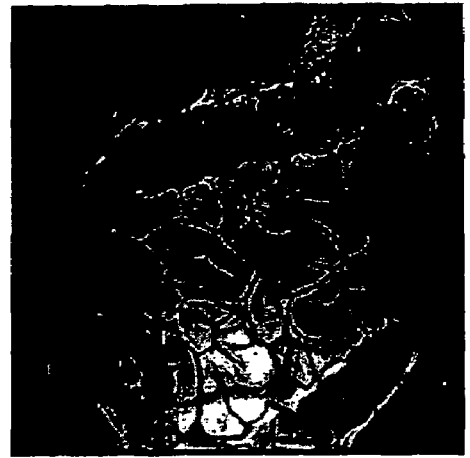
Figure 11:
Figure 11:
Figure 11:

The mere ingestion of water resulted in significantly less small bowel distension compared to water spiked with any of the four additives (p<0.01, FIG. 11). FIG. 11 shows coronal fast imaging with steady state precession (TrueFISP, TR/TE/flip 3.9/1.9/70°) of a volunteer undergoing five MR examinations ingesting different contrast agents: water (a), solution of 0.7% Metamucil (b), solution of 0.2% locust bean gum (c), solution of 2.5% mannitol (d) and a solution containing both 2.5% mannitol and 0.2% locust bean gum (e). The mere ingestion of water resulted in significantly less small bowel luminal fluid and less bowel distension compared to the ingestion of water spiked with any of the four additives. Of the four additives, the ingestion of water spiked with the combination of LBG and mannitol showed the best bowel distension.

Comparison of the four additives identified the combination of LBG and mannitol providing the highest small distension ($p<0.01$). The combination resulted in a mean small bowel diameter of 23.7 mm, compared to 21.3 mm with mannitol alone, 19.9 mm with LBG alone, and 16.6 mm with Metamucil. In one volunteer the application of LBG led to a greater distension than mannitol, while the combination of both substances showed the best distension in all volunteers. Table 2 summarizes these results.

TABLE 2

|  | #1 | #2 | #3 | #4 | #5 | #6 | AV |
|---|---|---|---|---|---|---|---|
| Water | 13.6 | 15.0 | 12.4 | 14.6 | 12.6 | 11.8 | 13.3 |
| (SD) | 2.6 | 3.0 | 2.6 | 2.2 | 3.1 | 2.9 |  |
| Metamucil | 18.2 | 15.6 | 15.3 | 18.1 | 16.6 | 15.9 | 16.6 |
| (SD) | 2.4 | 2.8 | 2.9 | 2.6 | 2.2 | 1.7 |  |
| Mannitol | 23.7 | 22.9 | 19.2 | 19.3 | 22.9 | 19.6 | 21.3 |
| (SD) | 3.6 | 4.0 | 2.6 | 2.7 | 3.1 | 1.8 |  |
| LBG | 21.3 | 19.5 | 20.2 | 19.4 | 20.7 | 18.2 | 19.9 |
| (SD) | 2.9 | 3.3 | 3.1 | 2.2 | 2.4 | 2.1 |  |
| Mannitol/LBG | 25.9 | 23.6 | 24.1 | 21.2 | 23.9 | 23.2 | 23.7 |
| (SD) | 3.6 | 3.5 | 3.2 | 3.3 | 4.1 | 3.0 |  |

Table 2: Mean small bowel diameters (in mm) and corresponding standard deviation. Last column on the right provides an overview over the average values of all six volunteer examinations.

The qualitative assessment of small bowel distension underscored the results of the quantitative evaluation. All examinations based on the mere ingestion of water were rated poorest, whereas the administration of combined mannitol and LBG provided the best distension in all six volunteers. Similarly Metamucil was ranked inferior to both mannitol and LBG alone. Differences between LBG and mannitol were less definitive: in four volunteers mannitol was rated better, while in the remaining two volunteers LBG was rated better.

The design of the presented study was based on practical parameters. The ingestion of 1500 ml of the described solution over 45 minutes did not negatively affect the volunteers. Side effects such as nausea were not reported. Of the three evaluated substances only mannitol alone consistently resulted in diarrhea. Both mannitol and LBG were found to be superior to Metamucil based on both the quantitative and qualitative analysis. Although very different in their mode of action, the difference between mannitol- and LBD-induced bowel distension was not significantly different. Combining the osmotic agent mannitol with the thickener locust bean gum resulted in the best distension: all portions of the small bowel were maximally dilated.

Example 5

Iodine—and barium—based oral contrast agents may introduce artefacts into the PET image in dual-modality PET/CT tomography. A negative oral contrast agent may prevent contrast-induced artefacts and improve PET/CT image quality. The following study introduced a solution containing 2.5% mannitol and 0.2% locust bean gum (LBG) as a negative oral contrast agent for PET/CT imaging. The purpose of the following study was to qualitatively and quantitatively assess the agent's ability to distend the stomach and the small bowel while avoiding PET artefacts in comparison to barium and water.

CT-PET examinations of 60 oncologic patients were performed on a combined CT-PET tomograph. Three different oral contrast agents were randomly assigned to 20 patients each: barium, water, and a solution of 2.5% mannitol and 0.2% locust bean gum (LBG). To compare the bowel distension abilities of the three agents, representative diameters each of the stomach, the jejunum and the ileum were measured by two radiologists. PET images were evaluated qualitatively for areas of increased bowel FDG uptake based on a four-point scale as well as quantitatively by determination of standard uptake values (SUV). To assess the effect of the different contrast agents onto the tracer activity concentration phantom measurements were performed.

Intestinal distension with LBG/mannitol proved better than water ($p<0.05$ to $p<0.001$) and barium ($p<0.001$). Quantitative analysis of the PET data revealed SUVs of 1.8 (+/−0.5) for LBG/mannitol, 1.7 (+/−0.5) for water, and 2.5 (+/−0.6) for barium. See Table 2. Qualitative evaluation of FDG uptake in the bowel demonstrated apparently increased glucose metabolism in the bowel lumen far more often with barium than with water or LBG/mannitol. Tracer activity concentration was overestimated with positive contrast agents. See Table 3.

Figure 12:
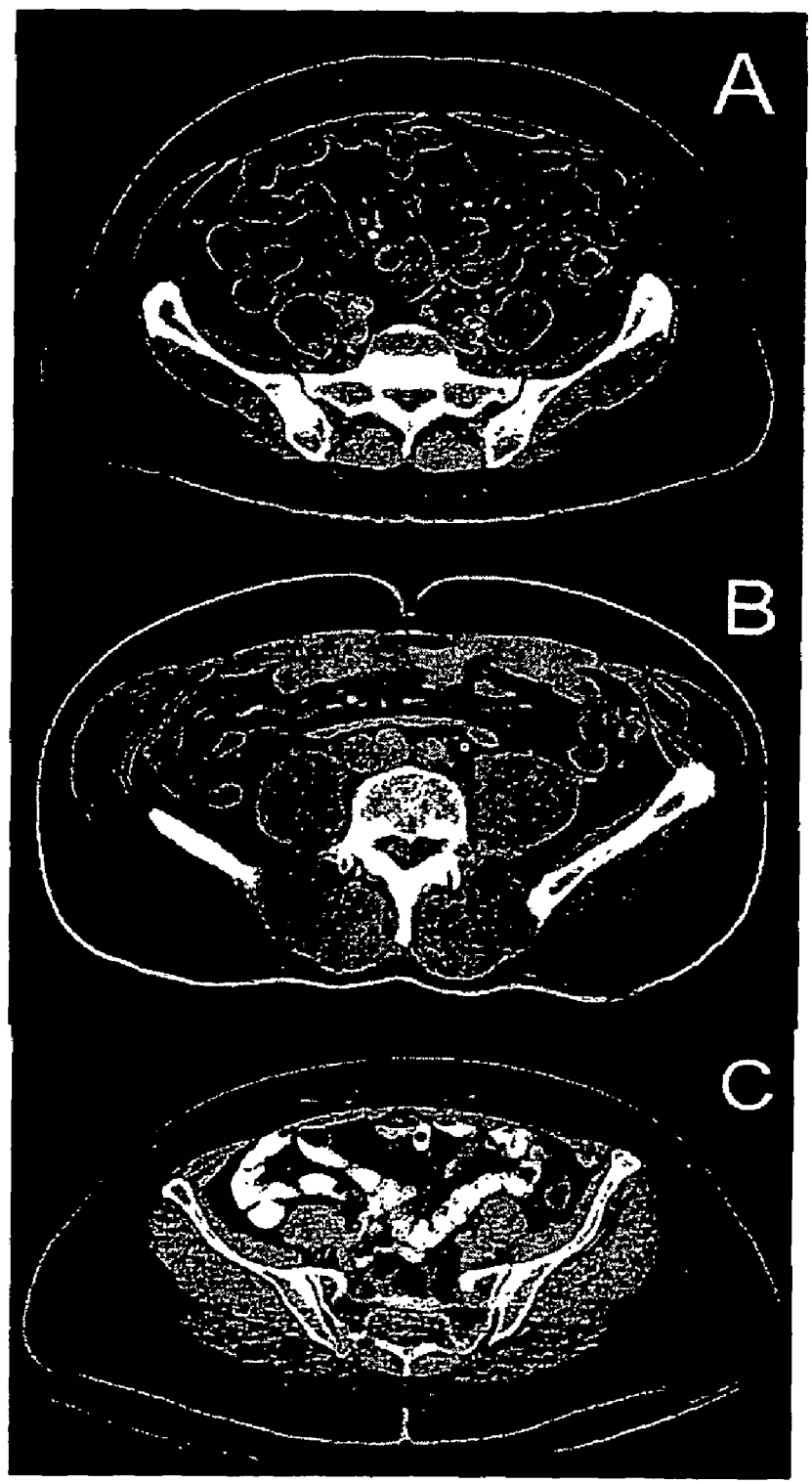
FIG. 12 shows difference degrees of intestinal distneion using various formulations.
Figure 13:
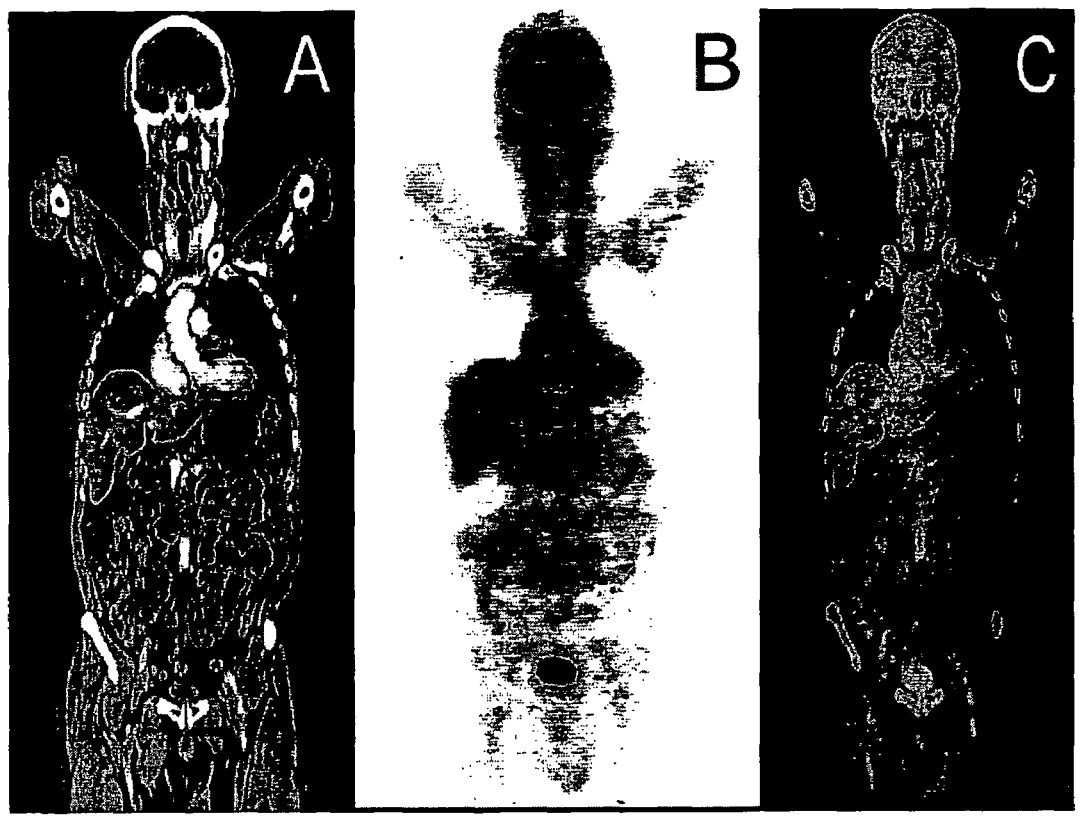
FIG. 13 shows CT, PET and fused PET/CT images of an individual.
Figure 14:
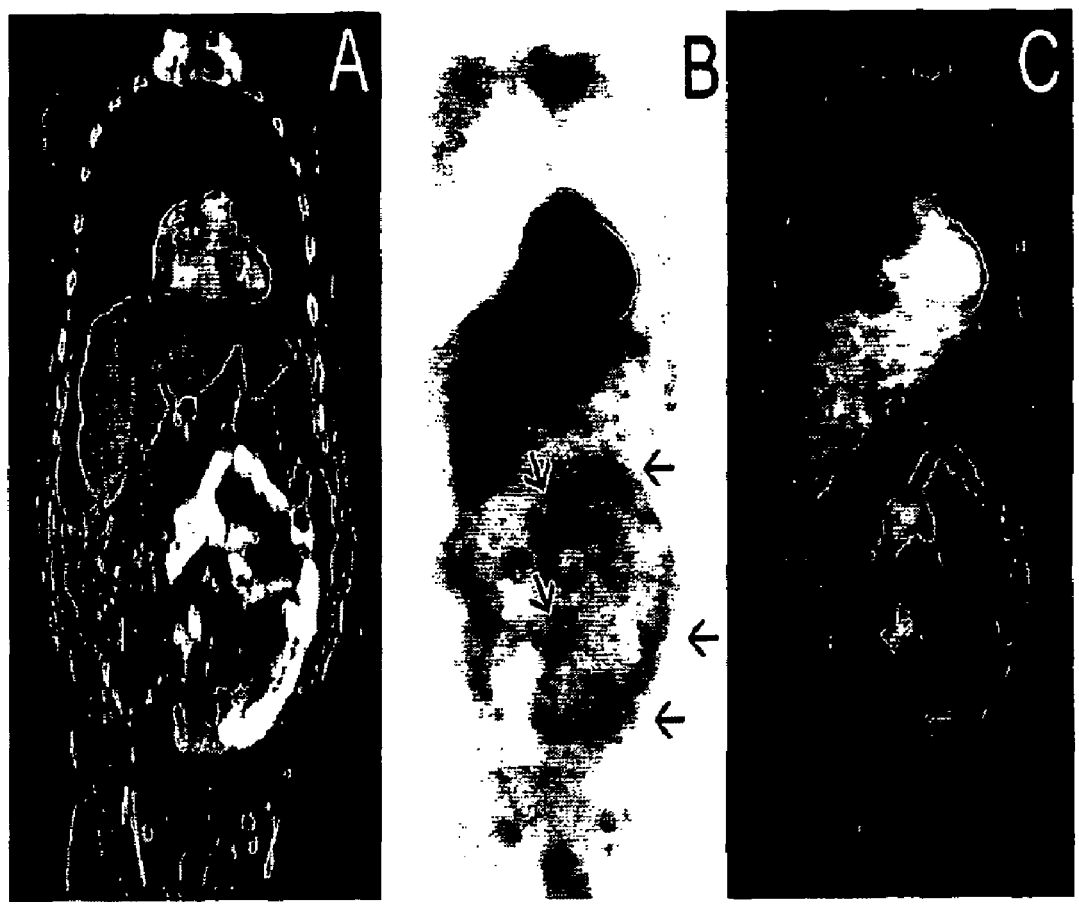
FIG. 14 shows CT, PET) and fused PET/CT images of an individual.

FIG. 12 shows different degrees of intestinal distension by the contrast agents under investigation. LBG/mannitol (A) led to superior and more homogeneous small bowel distension when compared to water (B) and barium (C). FIG. 13 shows CT (A), PET (B) and fused PET/CT images (C) of a patient after ingesting 2 liters of a solution containing LBG/mannitol for oral contrast. Homogeneous tracer uptake in the abdomen without contrast-induced artifacts is demonstrated on PET (B) and fused images (C). At the same time, the small bowel loops are easily delineated on the CT image (A). FIG. 14 shows CT (A), PET (B), and fused PET/CT images (C) in a patient undergoing PET/CT imaging with barium as an oral contrast agent. Apparent tracer uptake in co-registration with the bowel lumen can be detected on PET and fused data sets. Discrete physiologic FDG uptake can also be detected in the non-enhanced ascending colon.

It was concluded that LBG/mannitol may be used as a negative oral contrast agent in PET/CT imaging as it provides sufficient bowel distension while avoiding contrast-induced PET artefacts.

TABLE 3

|  | LBG/Mannitol | | Water | | Barium | | |
|---|---|---|---|---|---|---|---|
|  | Mean | SD | Mean | SD | Mean | SD | p-value |
| Stomach | 6.4 | 1.8 | 6.1 | 1.5 |  |  | 0.0401 |
|  | 6.4 | 1.8 |  |  | 5.0 | 1.1 | <0.001 |
|  |  |  | 6.1 | 1.5 | 5.0 | 1.1 | <0.001 |
| Jejunum | 2.1 | 0.3 | 1.6 | 0.3 |  |  | <0.001 |
|  | 2.1 | 0.3 |  |  | 1.9 | 0.3 | <0.001 |
|  |  |  | 1.6 | 0.3 | 1.9 | 0.3 | <0.001 |
| Ileum | 2.0 | 0.3 | 1.4 | 0.3 |  |  | <0.001 |
|  | 2.0 | 0.3 |  |  | 1.9 | 0.2 | <0.001 |
|  |  |  | 1.4 | 0.3 | 1.9 | 0.2 | <0.001 |
| SUV | 1.8 | 0.5 | 1.7 | 0.5 |  |  | 0.4002 |
|  | 1.8 | 0.5 |  |  | 2.5 | 0.6 | <0.001 |
|  |  |  | 1.7 | 0.5 | 2.5 | 0.6 | <0.001 |

Table 3 Intestinal distension of the stomach, the jejunum, and the ileum induced by the contrast agents under investigation as well as SUV of the small intestine in the presence of the different contrast materials. Statistical significance was determined by unpaired Student's test based on 200 measurements each for the stomach, the jejunum, the ileum, and the SUV. Thus, a total of 800 measurements were performed for every contrast agent under investigation.

TABLE 4

|  |  | LBG/Mannitol | Water | Barium |
|---|---|---|---|---|
| Qual. evaluation of FDG uptake | No | 12 | 10 | 5 |
|  | Mild | 7 | 7 | 10 |
|  | Moderate | 1 | 3 | 5 |
|  | Severe | 0 | 0 | 0 |
| Location of uptake | Lumen | 0 | 0 | 10 |
|  | Wall | 7 | 8 | 0 |
|  | Both | 1 | 2 | 5 |

Table 4: Qualitative evaluation of small intestinal tracer uptake in the presence of the three different oral contrast agents. The least amount of patients demonstrating intestinal FDG uptake was found with LBG/mannitol. FDG was found to be primarily in the bowel wall in LBG/mannitol and water, while with barium FDG uptake could be mainly coregistered with the bowel lumen.

The examples herein are presented for illustrative purposes only. They are not intended to limit the scope of the invention. Further, it should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be covered by the appended claims.

Also, the invention may suitably comprise, consist of or consist essentially of the elements described herein. Further, the invention illustratively disclosed herein suitably may be practiced in the absence of any element which is or is not specifically disclosed herein.

The invention claimed is:

1. A formulation for use in preparing for a medical or diagnostic procedure comprising: an aqueous solution of 0.005% to 0.5% by weight of a natural hydrocolloid stabilizing agent and 1% to 8% by weight of a sugar-based compound, wherein the formulation alters an anatomic segment for performance of the medical or diagnostic procedure by facilitating the transfer of fluid or semi-fluid into the anatomic segment or facilitating the inhibition of fluid re-absorption in the atomic segment, and by modifying the viscosity of the fluid or semi-fluid in the anatomic segment, wherein the natural hydrocolloid stabilizing agent consists essentially of locust bean gum and the sugar-based compound is selected from the group consisting of mannitol, sorbitol, and combinations thereof.

2. The formulation of claim 1, comprising about 0.05% to 0.5% by weight of the natural hydrocolloid.

3. The formulation of claim 1, further comprising natural or artificial flavoring.

4. A method of performing a diagnostic imaging procedure comprising administering the formulation of claim 1.

5. The method of claim 4, wherein the formulation is administered orally.

6. The method of claim 4, wherein the formulation is administered via intubation.

7. The method of claim 4, wherein said diagnostic imaging procedure further comprises imaging of the lymph nodes, vasculature system, pancreas, liver, appendix, gall bladder or spleen.

8. The method of claim 4, wherein said diagnostic imaging procedure further comprises imaging of the stomach.

9. The method of claim 4, wherein said diagnostic imaging procedure further comprises imaging of the gastrointestinal tract.

10. The method of claim 4, wherein said diagnostic imaging procedure comprises a technique selected from the group consisting of X-ray imaging, MR, CT, SPECT, PET and CT-PET.

11. The method of claim 10, further comprising the step of imaging the gastrointestinal tract.

12. The method of claim 10, further comprising the step of imaging the small intestine.

13. The method of claim 10, further comprising the step of imaging the colon.

14. The method of claim 10, further comprising the step of imaging the pancreas.

15. The method of claim 10, further comprising the step of imaging the duodenum.

16. The method of claim 10, further comprising the step of imaging the cecum.

17. The method of claim 10, further comprising the step of imaging the bowel.

18. The method of claim 10, further comprising the step of imaging the large intestine.

19. The method of claim 10, further comprising the step of imaging the jejunum.

20. The method of claim 10, further comprising the step of imaging the ileum.

21. The method of claim 10, further comprising the step of imaging the appendix.

22. The method of claim 10, further comprising the step of imaging the pancreas is imaged.

23. The method of claim 10, further comprising the step of imaging the duodenum.

24. The method of claim 10, further comprising the step of imaging the sigmoid.

25. The method of claim 10, further comprising the step of imaging the rectum.

26. The method of claim 10, further comprising the step of imaging the stomach.

27. The formulation of claim ,1 wherein the sugar-based compound is mannitol.

28. The formulation of claim 27, comprising about 0.25% by weight of the hydrocolloid and about 3% by weight mannitol.

29. A formulation comprising about 0.005% to 0.5% by weight locust bean gum and about 1% to 8% by weight mannitol.

* * * * *

UNITED STATES PATENT AND TRADEMARK OFFICE
CERTIFICATE OF CORRECTION

PATENT NO. : 7,427,391 B2  Page 1 of 1
APPLICATION NO. : 10/476314
DATED : September 23, 2008
INVENTOR(S) : Lauenstein et al.

It is certified that error appears in the above-identified patent and that said Letters Patent is hereby corrected as shown below:

Title Page:

Item (75) - Second Line: "Hubert Schneeman, Schermbeck (DE)"

should read

--Hubert Schneemann, Schermbeck (DE)--

Signed and Sealed this

Twenty-fourth Day of March, 2009

JOHN DOLL
*Acting Director of the United States Patent and Trademark Office*